(12) United States Patent
Migachyov et al.

(10) Patent No.: US 7,241,259 B2
(45) Date of Patent: *Jul. 10, 2007

(54) INTRAURETHRAL DEVICE AND METHOD

(75) Inventors: Valery Migachyov, San Antonio, TX (US); Tu T. Pham, San Antonio, TX (US)

(73) Assignee: Feelsure Health Corporation, Park Ridge, IL (US)

( * ) Notice: Subject to any disclaimer, the term of this patent is extended or adjusted under 35 U.S.C. 154(b) by 616 days.

This patent is subject to a terminal disclaimer.

(21) Appl. No.: 10/699,989

(22) Filed: Nov. 3, 2003

(65) Prior Publication Data

US 2004/0097786 A1  May 20, 2004

Related U.S. Application Data

(63) Continuation of application No. 09/908,467, filed on Jul. 18, 2001, now Pat. No. 6,676,593, which is a continuation of application No. 09/302,856, filed on Apr. 30, 1999, now abandoned.

(51) Int. Cl.
*A61F 2/00* (2006.01)
(52) U.S. Cl. ...................................... 600/29
(58) Field of Classification Search ............ 600/29–32; 128/DIG. 25, 833–839
See application file for complete search history.

(56) References Cited

U.S. PATENT DOCUMENTS

| | | | |
|---|---|---|---|
| 3,628,530 A | 12/1971 | Schwartz |
| 3,642,004 A | 2/1972 | Osthagen et al. |
| 3,812,841 A | 5/1974 | Isaacson |
| 4,246,896 A | 1/1981 | Horne, Jr. et al. |
| 4,553,533 A | 11/1985 | Leighton |
| 4,969,474 A | 11/1990 | Schwarz |
| 5,041,092 A | 8/1991 | Barwick |
| 5,078,676 A | 1/1992 | Bailly |
| 5,088,980 A | 2/1992 | Leighton |
| 5,090,424 A | 2/1992 | Simon et al. |
| 5,112,306 A | 5/1992 | Burton et al. |
| 5,114,398 A | 5/1992 | Trick et al. |
| 5,123,428 A | 6/1992 | Schwarz |
| 5,131,906 A | 7/1992 | Chen |
| 5,140,999 A | 8/1992 | Ardito |
| 5,234,409 A | 8/1993 | Goldberg et al. |
| 5,352,182 A | 10/1994 | Kalb et al. |
| 5,417,226 A | 5/1995 | Juma |
| 5,437,604 A | 8/1995 | Kulisz et al. |
| 5,479,945 A | 1/1996 | Simon |
| 5,483,976 A | 1/1996 | McLaughlin et al. |

(Continued)

FOREIGN PATENT DOCUMENTS

WO   WO 96/18431   6/1996

*Primary Examiner*—John P. Lacyk
(74) *Attorney, Agent, or Firm*—Crompton, Seager & Tufte LLC

(57) ABSTRACT

A device and method for treating female urinary incontinence is provided. A device in accordance with the invention includes a sheath having a distal portion, a proximal portion, and a lumen extending therebetween. A distal member is elastically hinged to the distal portion of the sheath. A flow control valve unit is disposed within a lumen of the sheath. The distal member may be urged into axial alignment with the sheath, and the device may be inserted into a female urethra. Once the device is inserted sufficiently distally into the female urethra, the distal member will return to a position which is not in axial alignment with the sheath.

30 Claims, 6 Drawing Sheets

U.S. PATENT DOCUMENTS

| | | |
|---|---|---|
| 5,509,888 A | 4/1996 | Miller |
| 5,618,257 A | 4/1997 | Kulisz et al. |
| 5,624,374 A | 4/1997 | Von Iderstein |
| 5,701,916 A | 12/1997 | Kulisz et al. |
| 5,704,353 A | 1/1998 | Kalb et al. |
| 5,707,357 A | 1/1998 | Mikhail et al. |
| 5,711,314 A | 1/1998 | Ardito |
| 5,713,829 A | 2/1998 | Hakky et al. |
| 5,722,932 A | 3/1998 | Kulisz et al. |
| 5,749,826 A | 5/1998 | Faulkner |
| 5,772,932 A | 6/1998 | Kamiguchi et al. |
| 5,795,288 A | 8/1998 | Cohen et al. |
| 5,800,339 A | 9/1998 | Salama |
| 5,806,527 A | 9/1998 | Borodulin et al. |
| 5,871,016 A | 2/1999 | Pham |
| 5,887,592 A | 3/1999 | Kulisz et al. |
| 6,676,593 B2 * | 1/2004 | Migachyov et al. .......... 600/29 |

* cited by examiner

INTRAURETHRAL DEVICE AND METHOD

This application is a continuation of U.S. patent application Ser. No. 09/908,467, filed on Jul. 18, 2001, now U.S. Pat. No. 6,676,593, which in turn is a continuation of U.S. patent application Ser. No. 09/302,856, filed on Apr. 30, 1999, now abandoned.

FIELD OF THE INVENTION

The present invention relates generally to devices and methods for treating female urinary incontinence. More particularly, the present invention relates to intraurethral devices and methods for controlling urine flow.

BACKGROUND OF THE INVENTION

Female urinary incontinence is a common medical condition, having widespread economic and social ramifications. The difficulty and embarrassment associated with urinary incontinence often causes the affected person to limit her social activities. In some cases, pads or diapers are used to absorb the uncontrolled seepage of urine. These absorbent items must be changed frequently, creating an ongoing economic burden. The wearing of absorbent undergarments may also restrict the type or style of clothing which the patient may wear. More seriously, skin irritation and other hygienic difficulties often result from the lingering presence of captured urine against tender urogenital tissues.

An additional method of treating urinary incontinence is the use of bladder flow control devices, sometimes referred to as artificial sphincters or prosthetic urethral valves. A bladder flow control device may be positioned in the. urethra of a patient to control the flow of urine out of the bladder. It is desirable for the placement of the bladder flow control apparatus in the urethra to be performed easily and non-surgically. Once the bladder flow control device is placed, it is desirable that it be safely and securely retained in the urethra. Optimally, the device surfaces which contact the human body. will be formed of biocompatible materials, to lessen chances of inflammation in patients.

SUMMARY OF THE INVENTION

The present invention relates generally to devices and methods for treating female urinary incontinence. More particularly, the present invention relates to an intraurethral device including a sheath having a distal portion and a proximal portion. The sheath includes a proximal retainer disposed proximate its proximal end. The proximal retainer serves to prevent distal motion of the sheath into the patient by lying against the urethral labia. The sheath further includes a sheath wall defining a central lumen. A flow control valve unit is disposed in the lumen of the sheath.

An intraurethral device in accordance with the present invention, further includes a distal member having a distal tip and a proximal portion. The proximal portion of the distal member is fixed to the distal portion of the sheath by a linking means. In one embodiment of the present invention, the linking means includes an elastomer hinge. When the elastomer hinge is in a natural, undeformed state, the central axis of the distal member of the intraurethral device is positioned at an angle to the central axis of the sheath. The distal member of the intraurethral device may be urged into axial alignment with the sheath by deforming the elastomer hinge.

In a presently preferred method in accordance with the present invention, the distal member is urged into axial alignment with the sheath during insertion of the intraurethral device into the urethra of a patient. In this presently preferred method, the intraurethral device is inserted into the urethra of the patient until the distal member is free to assume a misaligned position. In this misaligned position, the elastomer hinge assumes its natural, undeformed state. When the distal member of the intraurethal device assumes this misaligned position, the distal member serves to prevent proximal motion of the sheath out of the patient by contacting the bladder floor. Distal motion of the sheath into the patient is prohibited by the proximal retainer disposed at the proximal end of the sheath. In this manner, the intraurethral device is held within the urethra by the distal member and the proximal retainer acting at opposite ends of the urethra.

An insertion tool is also provided. The insertion tool includes a shaft having a distal end and a proximal end. The distal end of the shaft is adapted to selectively form a connection with a proximal end of the flow control valve unit disposed in the lumen of the sheath. The shaft of the insertion tool provides a convenient location to grasp the assembly. The use of an insertion tool minimizes the risk of infection by minimizing human contact with the intraurethral device.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
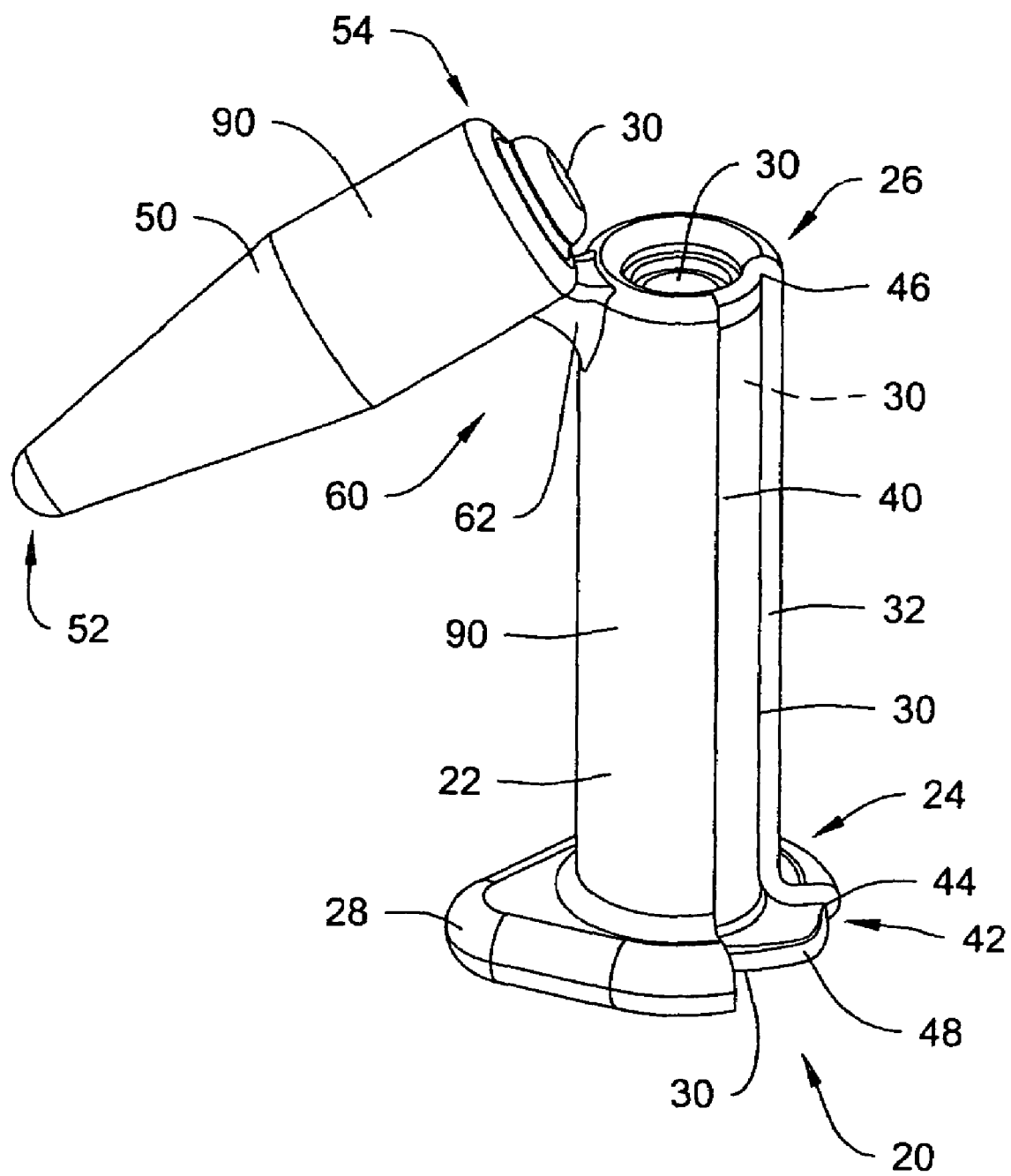
FIG. 1 is a perspective view of an intraurethral device in accordance with an exemplary embodiment of the present invention.

FIG. 1 is a perspective view of an intraurethral device 20 in accordance with the present invention. Intraurethral device 20 includes a sheath 22 having a distal portion 26 and a proximal portion 24. Sheath 22 also includes a proximal retainer 28 disposed proximate it's proximal portion 24. Proximal retainer 28 serves to prevent distal motion of sheath 22 into the patient by lying against the urethral labia. Sheath 22 includes a sheath wall 32 defining a central lumen 30.

A flow control valve unit 40 is disposed in lumen 30 of sheath 22. Two examples of flow control valve assemblies which are suitable for inclusion in valve housing 40 are described by Kulisz et al. in U.S. Pat. No. 5,437,604 entitled NONSURGICAL INTRAURETHRAL BLADDER CONTROL DEVICE, and U.S. patent application Ser. No. 09/207,821 by Migachyov and entitled VALVE FOR BLADDER CONTROL DEVICE, the disclosure of each being hereby incorporated by reference. Those of skill in the art will appreciate that other flow control valves may be used in conjunction with. intraurethral device 20 without departing from the spirit or scope of the present invention.

Proximal region 24 of sheath 22 includes a proximal lock 42 having recesses or cavities 44. Recesses 44 are adapted to receive a flange portion 48 of flow control valve unit 40. A distal stop 46 lies in distal region 26 of sheath 22 for arresting the distal movement of flow control valve unit 40. Sheath walls 32 are preferably formed of an elastomeric material such that a tubular flow control valve unit inserted within lumen 30 is partially held in position by a friction fit between the elastically stretched sheath walls 32 and the outside walls of the inserted flow control valve and/or by a medical grade adhesive.

Intraurethral device 20 also includes a distal member 50 having a distal tip 52 and a proximal portion 54. Proximal portion 54 of distal member 50 is fixed to distal portion 26 of sheath 22 by a linking means 60. In the embodiment of FIG. 1, linking means 60 includes an elastomer hinge 62.

When no external force is applied to elastomer hinge 62, intraurethral device 20 assumes the position illustrated in FIG. 1. Intraurethral device 20 may be selectively placed in other positions by deforming elastomer hinge 62. For example, distal member 50 may be urged into axial alignment with sheath 22. When intraurethral device 20 is in the position shown in FIG. 1, distal member 50 serves to prevent proximal motion of sheath 22 out of the patient by contacting the bladder floor. Two exemplary positions of distal member 50 are best illustrated in FIG. 2.

Figure 2:
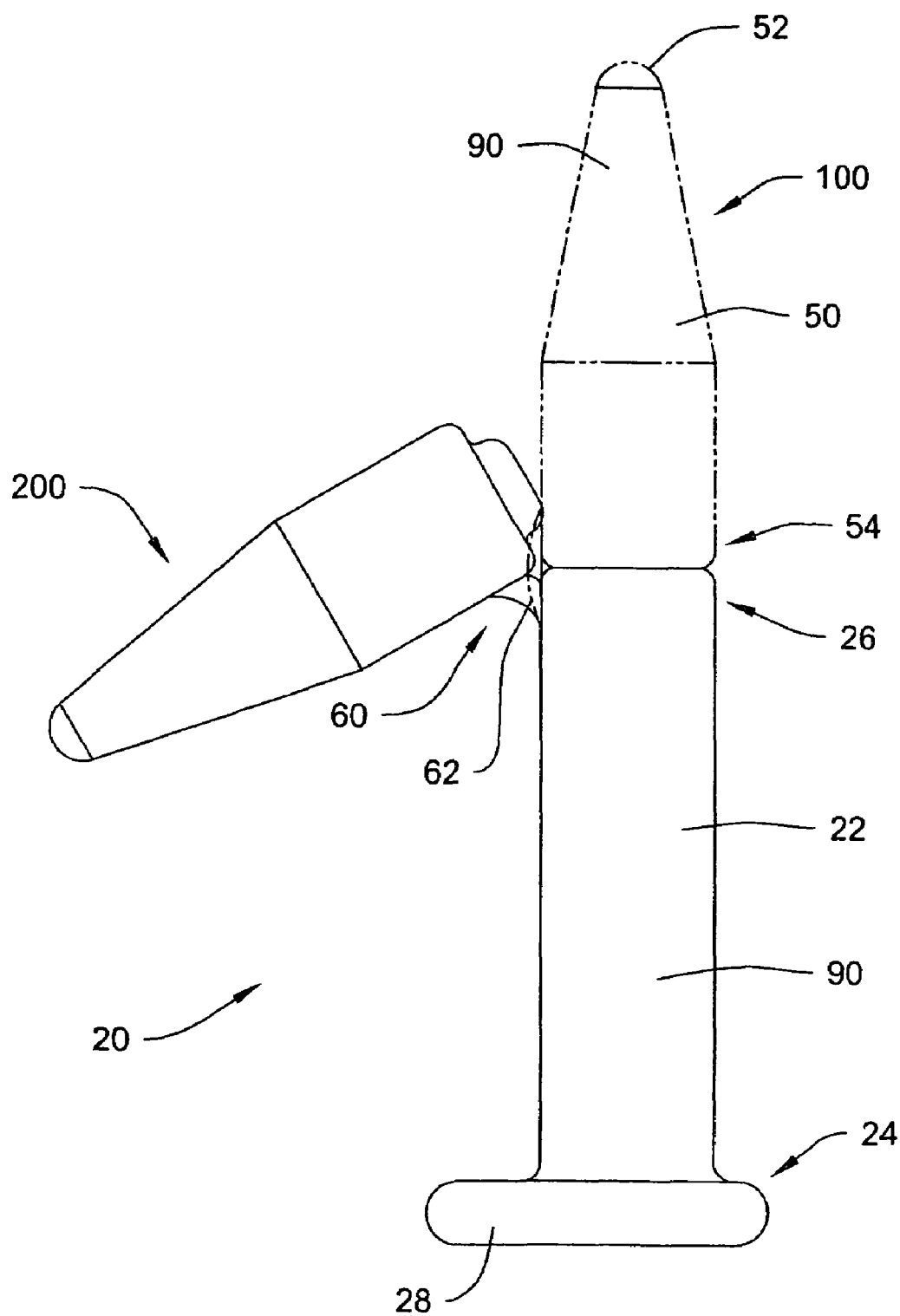
FIG. 2 is a side view of an intraurethral device in accordance with an exemplary embodiment of the present invention.

FIG. 2 is a plan view of intraurethral device 20 with an axially aligned position of distal member 50 shown with phantom lines. The axially aligned position of distal member 50 is generally designated by the number 100. In a presently preferred method in accordance with the present invention, intraurethral device 20 is urged into position 100 to aid in inserting intraurethral device 20 into a urethra. When no external forces are applied, intraurethral device 20 assumes a second position 200 as shown in FIG. 2. When intraurethral device 20 assumes second position 200, distal member 50 serves to prevent proximal motion of sheath 22 out of the patient by contacting the bladder floor. In this presently preferred method, intraurethral device 20 is inserted into the urethra of a patient until distal member 50 is free to assume a second position similar to position 200. Those of skill in the art will appreciate that elastomer hinge 62 may be deformed in varying degrees to achieve any number of second positions of distal member 50.

In a presently preferred embodiment, sheath 22, distal member 50, and elastomer hinge 62 are all comprised of the same material. A presently prefer-red method of manufacturing this preferred embodiment is injection molding. Materials which may be suitable for this preferred embodiment include implantable grade silicone rubber, and thermoplastic rubber. Single piece construction simplifies assembly and reduces the possibility of any device components separating during residence in the patient Embodiments of intraurethral device 20 have also been envisioned which include a surface layer 90. Surface layer 90 may include an anti-microbial chemical agent such as chlorhexidine gluconate (CHG) or silver compounds to reduce the likelihood of infection during use. Surface layer 90 may also include materials such as hyaluronic acid, a hydrogel, or other materials to mimic mucous. Surface layer 90 may also include a lubricious material such as a hydrophilic hydrogel or a hydrophobic silicone to facilitate insertion and removal. It is envisioned that one or more of the above described surface layer materials can be used. Embodiments of intraurethral device 20 have also been envisioned having a distal member 50 and a sheath 22 which are comprised of a material which includes the materials described above.

Figure 3:
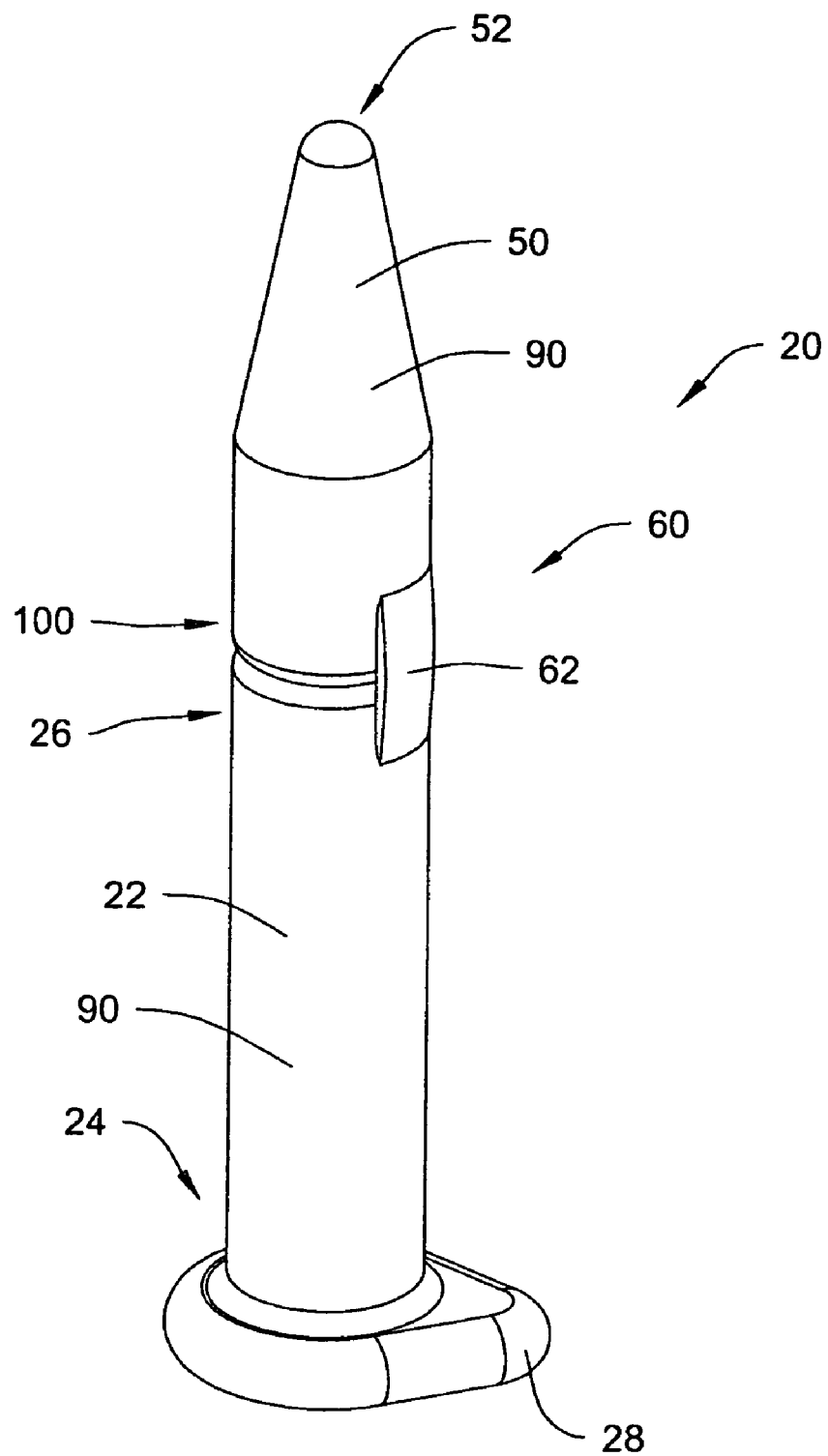
FIG. 3 is a perspective view of an intraurethral device in accordance with an exemplary embodiment of the present invention.

FIG. 3 is a perspective view of intraurethral device 20 with distal member 50 in axial alignment with sheath 22. In a presently preferred embodiment, distal member 50 preferably has a rounded shape to ease insertion through the urethra. Also in a presently preferred embodiment, the outer diameter of distal member 50 is substantially equal to the outer diameter of sheath 22.

In a presently preferred method distal member 50 is urged into position 100 when inserting sheath 22 into the urethra. This method may now be described with reference to FIGS. 1, 2, and 3. It should be understood that steps may be omitted from this process and/or, the sequence of the steps may be changed without deviating from the spirit or scope of the invention.

A presently preferred method in accordance with the present invention begins with the step of inserting distal member 50 into a female urethra. Intraurethral device 20 is then urged into position 100 as shown in FIGS. 2 and 3. The remainder of intraurethral device 20 including sheath 22 may then be urged into the female urethra. In many cases it is desirable to apply a lubricant to the exterior surfaces of distal member 50 and sheath 22 prior to insertion. During this insertion step, the urethra will hold intraurethral device 20 in position 100 until distal portion 50 enters the bladder. After distal portion 50 of intraurethral device 20 enters the bladder, it will be free to assume position 200. When intraurethral device 20 assumes first position 200, distal member 50 serves to prevent proximal motion of sheath 22 out of the patient by contacting the bladder floor. As mentioned previously, elastomer hinge 62 is biased to place distal portion 50 in first position 200.

Figure 4:
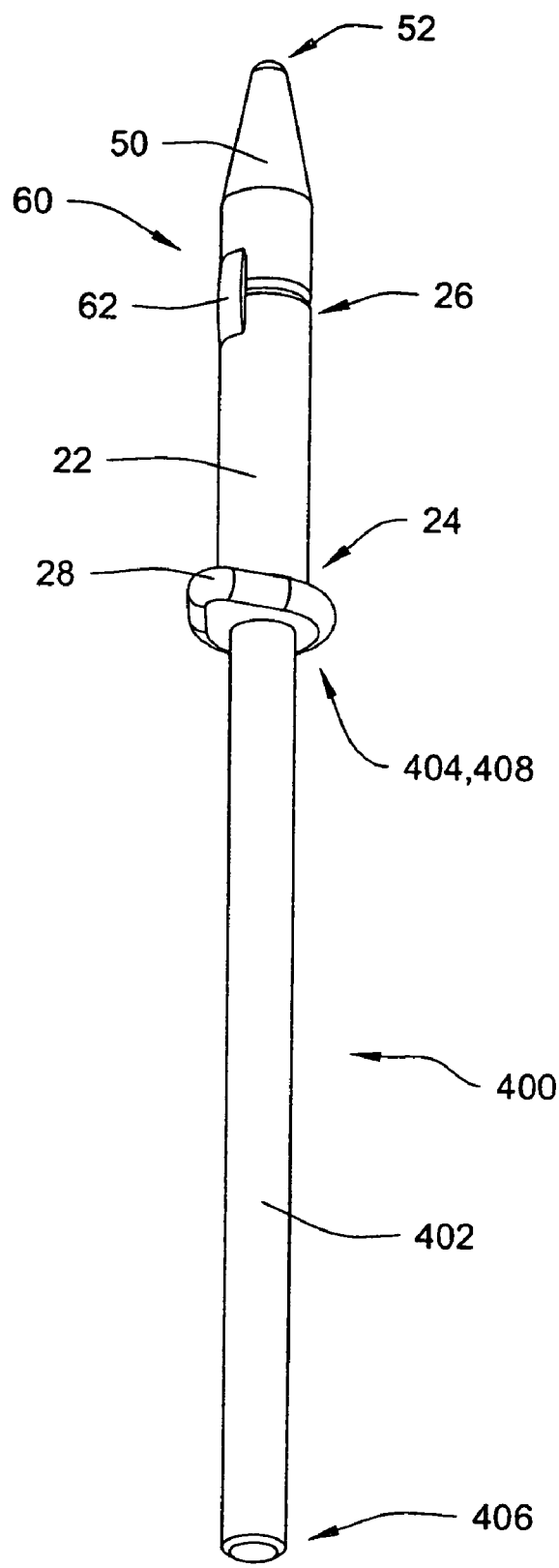
FIG. 4 is a perspective view of an assembly including an insertion tool and an intraurethral device in accordance with an exemplary embodiment of the present invention.

FIG. 4 is a perspective view of an assembly including an intraurethral device 20 and an insertion tool 400. Insertion tool 400 includes a shaft 402 having a distal end 404 and a proximal end 406. In the embodiment of FIG. 4 a distal portion 408 of insertion tool 400 is disposed in lumen 30 of sheath 22. A lumen 30 (shown in FIG. 1) extends into proximal portion 54 of tip 52.

Proximal portion 54 of distal member 50 is fixed to distal portion 26 of sheath 22 by a linking means 60. In the embodiment of FIG. 4, linking means 60 includes an elastomer hinge 62. A distal end 404 of insertion tool 400 is disposed in lumen 30 of distal member 50. As shown in FIG. 4, distal member 50 is held in axial alignment with sheath 22 by the presence of distal end 404 of shaft 402 in lumen 30 of distal member 50.

A method of positioning an intraurethral device 20 into a urethra using insertion tool 400 may now be described with reference to FIG. 4. A first step desirable in some applications is to pre-lubricate and pre-dilate the urethra of the patient. The use of insertion tool 400 begins with the step of inserting distal end 404 of shaft 402 into lumen 30 of sheath 22. Distal portion 50 of intraurethral device 20 is then urged into axial alignment with sheath 22. As a result, lumen 30 of distal portion 50 is disposed in axial alignment with lumen 30 of sheath 22. Insertion tool 400 may then be urged forward so that distal end 404 enters lumen 430 of distal portion 50. The entire assembly may now be held by grasping shaft 402 of insertion tool 400. When insertion tool 400 is disposed within lumen 30 of sheath 22 and distal portion 50 it provides structural support. The structural support provided by insertion tool 400 improves the pushability of sheath 22 and distal member 50. Distal member 50 and sheath 22 may now be inserted into the urethra. In may cases it is desirable to apply a lubricant to the exterior surfaces of distal member 50 and sheath 22 prior to insertion.

Having placed intraurethral device 20 into the urethra, insertion tool 400 may now be removed from lumen 30 of sheath 22. This may be accomplished by applying a pulling force on shaft 402 of insertion tool 400 while applying a pushing force on proximal retainer 28 of intraurethral device 20. When insertion tool 400 is removed, distal portion 50 of intraurethral device 20 will be free to assume position 200 as shown in FIG. 2. When intraurethral device 20 assumes position 200, distal member 50 serves to prevent proximal motion of sheath 22 out of the patient by contacting the bladder floor. Distal motion of sheath 22 into the patient is prohibited by proximal retainer 28.

With sheath 22 and distal member 50 now in the desired position, flow control Valve unit 40 may now be inserted into lumen 30 of sheath 22. One method suitable for inserting a flow control valve unit into a sheath is described by Pham in U.S. Pat. No. 5,871,016 entitled BLADDER CONTROL DEVICE RETAINER AND METHOD, the disclosure of which is hereby incorporated by reference. This U.S. patent is commonly assigned with the present application.

In the foregoing method, shaft 402 of insertion tool 400 provides a convenient location to grasp with the fingers. The use of insertion tool 400 minimizes the risk of infection by minimizing human contact with intraurethral device 20.

Other embodiments of insertion tool 400 are possible without deviating from the spirit or scope of the present invention. Specifically, in a presently preferred embodiment, distal end 404 of shaft 402 is adapted to releasably mate with the proximal end of flow control valve unit 40. A method of inserting an intraurethral device 20 in a urethra utilizing this presently preferred embodiment of insertion tool 400 may now be described with reference to FIGS. 1 and 4. This method typically begins with the step of inserting flow control valve 40 into lumen 30 of sheath 22. An additional step in this method is releasably mating the distal end 404 of shaft 402 with the proximal end of flow control valve unit 40. In some instances, it may be desirable to reverse the order of these steps since insertion tool 400 may aid in inserting flow control valve unit 40 into lumen 30 of sheath 22.

When flow control valve 40 is inserted completely into lumen 30 of sheath 22, flange 48 may be inserted into recesses 44. With the distal end of insertion tool 400 mated to the proximal end of flow control valve unit 40, shaft 402 of insertion tool 400 provides a convenient location to grasp the assembly. The use of insertion tool 400 minimizes the risk of infection by minimizing human contact with intraurethral device 20.

Shaft 402 of insertion tool 400 may be grasped with the physicians fingers to begin insertion of intraurethral device 20 is inserted into the urethra. Distal member 50 of intraurethral device 20 may then be inserted into the urethra of the patient. Having positioned distal member 50 in the urethra, intraurethral device 20 is then urged into position 100 as shown in FIGS. 2 and 3. The remainder of intraurethral device 20 including sheath 22 may then be urged into the female urethra. During this insertion step, the urethra will hold intraurethral device 20 in position 100 until distal portion 50 enters the bladder. After distal portion 50 of intraurethral device 20 enters the bladder, it will be free to assume position 200. When intraurethral device 20 assumes first position 200, distal member 50 serves to prevent proximal motion of sheath 22 out of the patient by contacting the bladder floor. As mentioned previously, elastomer hinge 62 is biased to place distal portion 50 in first position 200.

Once intraurethral device 20 is located in the desired position, the distal end of insertion tool 400 may be disengaged from the proximal end of flow control valve unit 40. Those of skill in the art will appreciate that a number of methods may be used to releasably mate distal end 404 of shaft 402 to the proximal end of the flow control valve unit 40. Examples of methods suitable for some applications include screw threads, a bayonet connection, and an interference fit.

Figure 5:
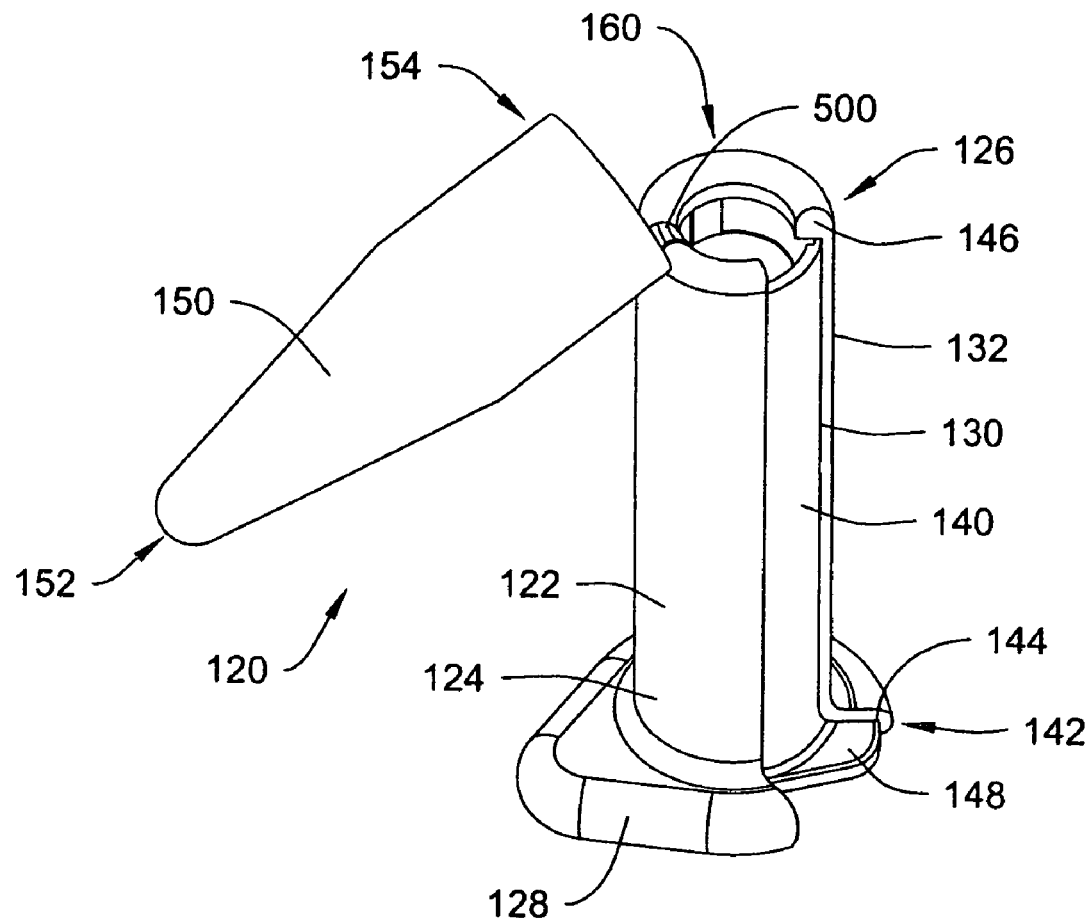
FIG. 5 is a perspective view of an additional embodiment of an intraurethral device in accordance with the exemplary embodiment of the present invention.

FIG. 5 is a perspective view of an additional embodiment of an intraurethral device 120 in accordance with the present invention. Intraurethral device 120 includes a sheath 122 having a distal portion 126 and a proximal portion 124. Sheath 122 also includes a proximal retainer 128 disposed proximate it's proximal portion 124. Sheath 122 includes a sheath wall 132 defining a central lumen 130, providing a fluid flow channel from a distal orifice 136 to a proximal orifice 134 in proximal region 124.

A flow control valve unit 140 is disposed in lumen 130 of sheath 122. Proximal region 124 includes a proximal lock 142 having recesses or cavities 144. Recesses 144 are adapted to receive a flange portion 148 of flow control valve unit 140. A distal stop 146 lies in distal region 126 for arresting the distal movement of flow control valve unit 140. Sheath walls 132 are preferably formed of an elastomeric material such that a tubular flow control valve unit inserted within lumen 130 is partially held in position by a friction fit between the elastically stretched sheath walls 132 and the outside walls of the inserted flow control valve.

Intraurethral device 120 also includes a distal member 150 having a distal tip 152 and a proximal portion 154. Proximal portion 154 of distal member 150 is fixed to distal portion 126 of sheath 122 by a linking means 160. In the embodiment of FIG. 5, linking means 160 includes a leaf spring 500. In a presently preferred embodiment, leaf spring 500 is comprised of stainless steel. Those of skill in the art will appreciate that leaf spring 500 may be comprised of other materials without deviating from the spirit and scope of the present invention.

Intraurethral device 120 assumes the position illustrated in FIG. 5, whenever no outside forces are acting upon leaf spring 500. Intraurethral device 120 may be selectively placed in other positions by applying force to deform leaf spring 500. For example, distal member 150 may be urged into axial alignment with sheath 122. When intraurethral device 120 is in the position shown in FIG. 5, distal member 150 serves to prevent proximal motion of sheath 122 out of the patient by contacting the bladder floor. Distal member 150 may be selectively positioned in axial alignment with sheath 122.

In a presently preferred embodiment, distal member 150 and leaf spring 500 are fixed together using an over molding process. In the manufacturing process, a distal portion of leaf spring 500 is positioned in a mold cavity. The material of distal member 150 is then injected into the mold cavity. The material of distal member 150 surrounds distal portion of leaf spring 500. Materials which may be suitable for this preferred embodiment include thermoset materials such as implantable grade silicone rubber. Materials which may be suitable for this preferred embodiment also include thermoplastic materials such as thermoplastic rubber. Those of skill in the art will appreciate that other methods of attaching distal portion 502 of leaf spring 500 to distal member 150 may be used without deviating from the spirit or scope of the present invention. For example, the mechanical attachment or the use of adhesives may be suitable for some applications.

In the embodiment of FIG. 5, a proximal portion of leaf spring 500 is fixed to sheath 122. A number of methods may be used to attach proximal portion 154 to sheath 122, including over-molding, adhesive bonding, and mechanical attachment. Additional embodiments have been envisioned in which proximal portion of leaf spring 500 is fixed to flow control valve unit 140.

When insertion tool 400 is removed, distal portion 150 of intraurethral device 120 will be free to assume position 200 as shown in FIG. 2. When intraurethral device 120 assumes position 200, distal member 150 serves to prevent proximal motion of sheath 122 out of the patient by contacting the bladder floor. Distal motion of sheath 122 into the patient is prohibited by proximal retainer 128.

Figure 6:
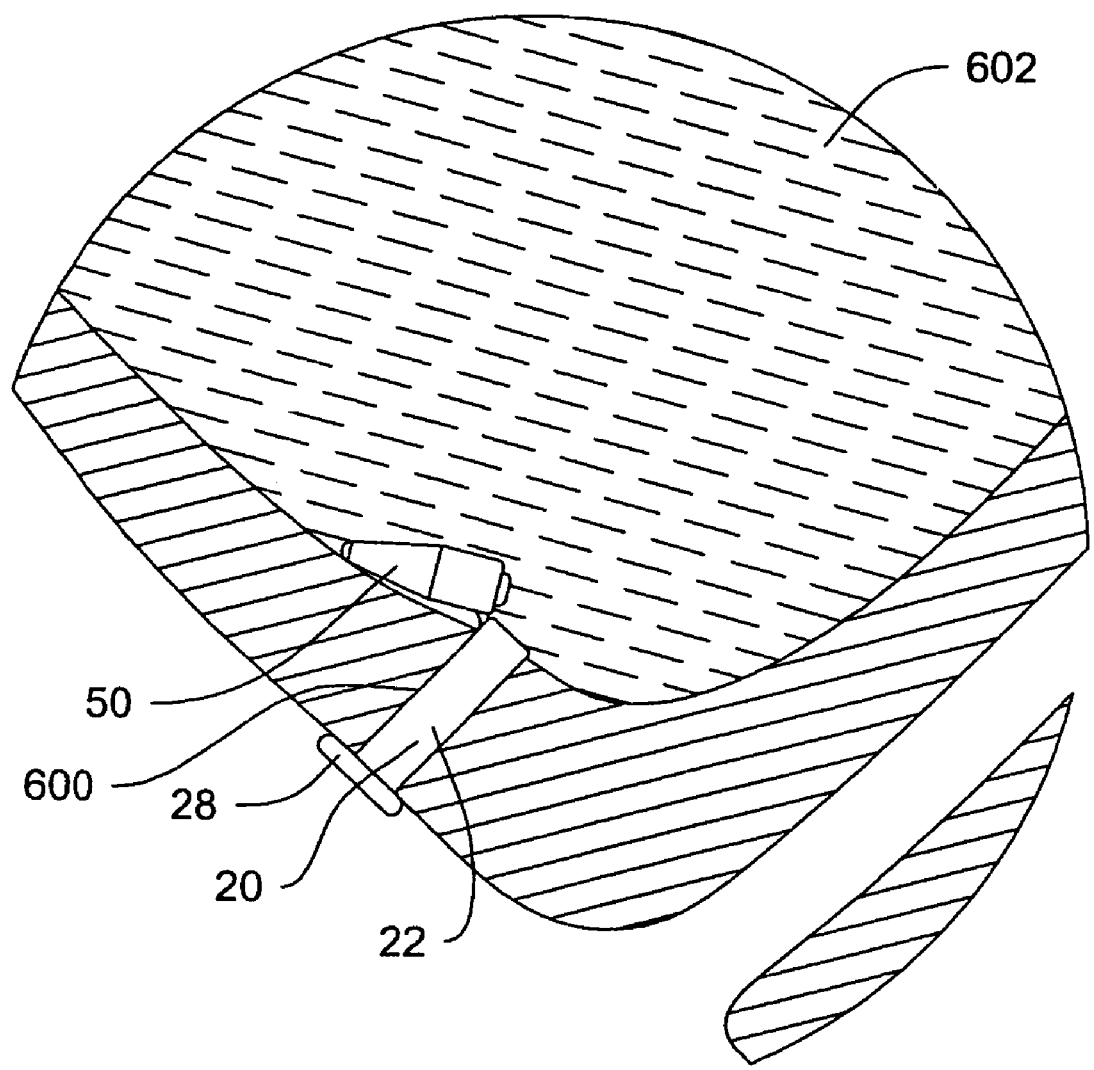
FIG. 6 is a side view of an intraurethral device disposed in the urethra of a patient.

Referring now to FIG. 6 there is shown a partial cross-sectional view representative of a urethra 600 and a bladder 602 of a patient. In FIG. 6 intraurethral device 20 is shown after placement in the urethra of the patient. and after whatever placement devices which were used have been removed and the urethra has undilated to closely hold and form to the outer surface of intraurethral device 20. It can be appreciated that after intraurethral device 20 is placed in the desired position distal portion 50 of intraurethral device 20 assumes a position which is not in axial alignment with sheath 22. When intraurethral device 20 assumes such a position, distal member 50 serves to prevent proximal motion of sheath 22 out of the patient by contacting the bladder floor. Distal motion of sheath 22 into the patient is prohibited by proximal retainer 28 which contacts the labia of the urethra. In this manner, intraurethral device 20 is held within the urethra by distal member 50 and proximal retainer 28 acting at opposite ends of the urethra.

Having thus described the preferred embodiments of the present invention, those of skill in the art will readily appreciate that yet other embodiments may be made and used within the scope of the claims hereto attached.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An intraurethral device, comprising:
   a sheath having a distal portion, a proximal portion, and a lumen therethrough;
   a urinary flow control valve disposed within the lumen of said sheath;
   a distal member having a distal portion and a proximal portion, the proximal portion of the distal member being operatively connected to the distal portion of the sheath; and
   a proximal retainer disposed on the proximal portion of the sheath;
   wherein the distal member and the sheath each define a longitudinal axis, wherein the longitudinal axis of the distal member is disposed at an angle relative to the longitudinal axis of the sheath.

2. The intraurethral device of claim 1, wherein the distal member is actuatable between a first, outwardly extended position and a second, longitudinally extended position.

3. The intraurethral device of claim 1, wherein the distal member defines a lumen.

4. The intraurethral device of claim 3, further comprising means for axially aligning the lumen of the distal member with the lumen of the sheath.

5. The intraurethral device of claim 4, wherein said means for axially aligning the lumen of the distal member with the lumen of the sheath includes an insertion tool.

6. The intraurethral device of claim 1, wherein the distal portion of said distal member is generally conical in shape.

7. The intraurethral device of claim 1, wherein the outer diameter of said distal member is substantially equal to the outer diameter of said sheath.

8. The intraurethral device of claim 1, wherein the sheath and distal member are both comprised of silicon rubber.

9. The intraurethral device of claim 1, wherein the sheath and distal member are both comprised of thermoplastic rubber.

10. The intraurethral device of claim 1, further comprising linking means for hingedly connecting the proximal portion of the distal member to the distal portion of the sheath.

11. The intraurethral device of claim 10, wherein said linking means includes an elastomeric hinge.

12. The intraurethral device of claim 10, wherein said linking means includes a leaf spring.

13. The intraurethral device of claim 1, wherein the proximal retainer includes a proximal lock.

14. The intraurethral device of claim 13, wherein said proximal lock includes a plurality of recesses or cavities adapted to receive a flanged portion of said urinary flow control valve.

15. The intraurethral device of claim 1, wherein the distal portion of said sheath includes a distal stop configured to prevent distal movement of the urinary flow control valve.

16. An intraurethral device, comprising:
   a sheath having a distal portion, a proximal portion, and a lumen therethrough;
   a urinary flow control valve disposed within the lumen of said sheath;
   a distal member having a distal portion and a proximal portion, the proximal portion of the distal member being hingedly connected to the distal portion of the sheath; and
   a proximal retainer disposed on the proximal portion of the sheath.

17. An intraurethral bladder control assembly, comprising:
   a sheath having a distal portion, a proximal portion, and a lumen therethrough;
   a urinary flow control valve disposed within the lumen of said sheath;
   a distal member having a distal portion and a proximal portion, the distal member being actuatable between a first, outwardly extended position and a second, longitudinally extended position; and an insertion tool for axially aligning the distal member with the sheath;

wherein the distal member is coaxially aligned with the sheath in the longitudinally extended position.

18. The intraurethral bladder control assembly of claim 17, wherein the distal portion of said distal member is generally conical in shape.

19. The intraurethral bladder control assembly of claim 17, wherein the outer diameter of said distal member is substantially equal to the outer diameter of said sheath.

20. The intraurethral bladder control assembly of claim 17, wherein the sheath and distal member are both comprised of silicon rubber.

21. The intraurethral bladder control assembly of claim 17, wherein the sheath and distal member are both comprised of thermoplastic rubber.

22. The intraurethral bladder control assembly of claim 17, further comprising linking means for hingedly connecting the proximal portion of the distal member to the distal portion of the sheath.

23. The intraurethral bladder control assembly of claim 22, wherein said linking means includes an elastomeric hinge.

24. The intraurethral bladder control assembly of claim 22, wherein said linking means includes a leaf spring.

25. The intraurethral bladder control assembly of claim 17, wherein the proximal portion of said sheath includes a proximal lock.

26. The intraurethral bladder control assembly of claim 25, wherein said proximal lock includes a plurality of recesses or cavities adapted to receive a flanged portion of said urinary flow control valve.

27. The intraurethral devise bladder control assembly of claim 17, wherein the distal portion of said sheath includes a distal stop configured to prevent distal movement of the urinary flow control valve.

28. An intraurethral bladder control assembly, comprising:

a sheath having a distal portion, a proximal portion, and a lumen therethrough;

a urinary flow control valve disposed within the lumen of said sheath;

a distal member having a distal portion, a proximal portion, and a lumen, the distal member being actuatable between a first, outwardly extended position and a second, longitudinally extended position; and an insertion tool for axially aligning the lumen of the distal member with the lumen of the sheath.

29. The intraurethral device of claim 1, wherein the flow control valve includes a flanged portion and the proximal retainer includes a proximal lock having a plurality of recesses or cavities adapted to receive the flanged portion of the flow control valve.

30. The intraurethral device of claim 16, wherein the flow control valve includes a flanged portion and the proximal retainer includes a proximal lock having a plurality of recesses or cavities adapted to receive the flanged portion of the flow control valve.

* * * * *